US009018421B2

(12) United States Patent
Gayet et al.

(10) Patent No.: US 9,018,421 B2
(45) Date of Patent: Apr. 28, 2015

(54) SEPARATION OF AROMATIC ALDEHYDES

(75) Inventors: Hubert Gayet, Villeurbanne (FR); Jean-Claude Masson, Lyons (FR)

(73) Assignee: Rhodia Operations, Aubervilliers (FR)

( * ) Notice: Subject to any disclaimer, the term of this patent is extended or adjusted under 35 U.S.C. 154(b) by 920 days.

(21) Appl. No.: 13/054,746

(22) PCT Filed: Jul. 17, 2009

(86) PCT No.: PCT/EP2009/059226
§ 371 (c)(1),
(2), (4) Date: Jun. 6, 2011

(87) PCT Pub. No.: WO2010/007161
PCT Pub. Date: Jan. 21, 2010

(65) Prior Publication Data
US 2012/0103786 A1   May 3, 2012

(30) Foreign Application Priority Data

Jul. 18, 2008   (FR) ..................... 08 04103

(51) Int. Cl.
*C07C 45/82* (2006.01)
*B01D 1/22* (2006.01)
*C07C 45/80* (2006.01)
*B01D 3/14* (2006.01)

(52) U.S. Cl.
CPC . *C07C 45/82* (2013.01); *B01D 1/22* (2013.01); *C07C 45/80* (2013.01); *B01D 3/148* (2013.01)

(58) Field of Classification Search
USPC .......................................... 568/479; 203/77
See application file for complete search history.

(56) References Cited

U.S. PATENT DOCUMENTS

| | | | |
|---|---|---|---|
| 4,090,922 A | 5/1978 | Bauer et al. | |
| 4,482,433 A | 11/1984 | Drake | |
| 5,294,406 A | 3/1994 | Sekido et al. | |
| 6,562,996 B2 | 5/2003 | Saleh et al. | |
| 2006/0211880 A1 | 9/2006 | Ackerman et al. | |

FOREIGN PATENT DOCUMENTS

| | | |
|---|---|---|
| CN | 1109861 A | 10/1995 |
| CN | 1112545 A | 11/1995 |
| CN | 2551311 Y | 5/2003 |
| CN | 101209959 A | 7/2008 |
| DE | 2930222 A1 | 2/1981 |
| FR | 1040559 | 10/1953 |
| FR | 1043070 | 11/1953 |
| FR | 2253542 A1 | 7/1975 |
| GB | 401562 | 11/1933 |
| GB | 2055795 A | 3/1981 |
| JP | S 55-62036 A | 5/1980 |
| JP | S 56-20538 A | 2/1981 |
| JP | 2003-183268 A | 7/2003 |
| WO | WO 2004063140 A1 | 7/2004 |

OTHER PUBLICATIONS

International Search Report corresponding to PCT/EP 2009/059226 mailed Sep. 22, 2009.
Vidal, J.-P., 2006. "Vanillin" in Kirk-Othmer Encyclopedia of Chemical Technology. Available at http://onlinelibrary.wiley.com/doi/10.1002/0471238961.2201140905191615.a01.pub2/pdf—14 pages.

*Primary Examiner* — Sikarl Witherspoon
(74) *Attorney, Agent, or Firm* — Beatrice C. Ortego

(57) ABSTRACT

A method for separating and recovering an aromatic aldehyde from a mixture thereof that also contains tar and light and heavy impurities, includes feeding the liquid flow containing this mixture into an evaporator, vaporizing the mixture in order to separate, on the one hand, a gaseous flow containing the aromatic aldehyde, the light impurities, the heavy impurities that can be vaporized at the selected evaporation temperature and pressure and, on the other hand, a liquid flow essentially containing the tar, and recovering the aromatic aldehyde from the separated gaseous flow.

22 Claims, 4 Drawing Sheets

SEPARATION OF AROMATIC ALDEHYDES

CROSS-REFERENCE TO PRIOR APPLICATIONS

This application claims priority under 35 U.S.C. §119 of FR 0804103, filed Jul. 18, 2008, and is the U.S. National Stage of PCT/EP 2009/059226, filed Jul. 17, 2009 and designating the United States (published in the French language on Jan. 21, 2010, as WO 2010/007161 A1; the title and abstract were also published in English), each hereby expressly incorporated by reference in its entirety and each assigned to the assignee hereof.

The subject of the present invention is a process for separating an aromatic aldehyde from a mixture that also contains tar.

More particularly the invention relates to the separation of a hydroxy- and/or alkoxy-aromatic aldehyde.

The invention is more particularly directed toward the treatment of tar resulting from a process for preparing and purifying vanillin (4-hydroxy-3-methoxybenzaldehyde) and ethylvanillin (3-ethoxy-4-hydroxybenzaldehyde).

Hydroxy- and/or alkoxyaromatic aldehydes are very important products used first as flavors and fragrances and then subsequently as intermediate products in many fields, for instance agrochemistry, pharmacy, the cosmetics industry and other industries.

In particular, vanillin and ethylvanillin are products that are essentially intended for foodstuffs. It is therefore important to propose, on the market, products of high chemical purity and of good taste quality.

Thus, the process for synthesizing them requires separation and thorough purification operations.

Various processes have been proposed for the synthesis of aromatic aldehydes.

The most important processes are based on the functionalization of a starting phenolic compound, for example phenol, catechol, catechol derivative, guaicol (or 2-methoxyphenol) and guethol (or 2-ethoxyphenol).

Generally, in this type of process, the phenolic compound is in a salified form, for example in the form of a sodium salt: a formyl group is added in the para-position with respect to the hydroxyl group present on the benzene ring, according to various methods.

A process for preparing in particular vanillin has been proposed in EP-A-0 773 919, said process consisting in reacting formaldehyde and guaicol in the presence of sodium hydroxide, resulting in a mixture comprising o-hydroxymethylguaicol (OMG), p-hydroxymethylguaicol (PMG) and 4,6-di(hydroxymethyl)guaicol (DMG), then in oxidizing said mixture with oxygen in the presence of a palladium catalyst and of a bismuth catalyst and in subsequently eliminating, in the oxidation products comprising it, the carboxyl group located in the ortho position, thus making it possible to obtain vanillin with a good reaction yield.

Furthermore, there exists a completely different route for access to vanillin which consists in reacting guaicol and glyoxylic acid in a basic medium, resulting in 4-hydroxy-3-methoxymandelic acid, and then in oxidizing the condensate obtained.

At the end of the oxidation reaction, the precursor of vanillin, i.e. the hydroxyl group is in salified form, preferably in sodium salt form, the excess guaicol, also in salified form, and various impurities are obtained.

In a subsequent step, the vanillin and the guaicol present in the reaction medium are released by acidification carried out using a strong acid, for example sulfuric acid.

For separating the vanillin from the crude reaction mixture, a known method consists in extracting it using an organic solvent.

For isolating the vanillin from the extraction solvent, a distillation of said mixture is carried out, making it possible to obtain, at the distillation top, the extraction solvent (which is the most volatile compound of the mixture) and, at the distillation bottom, a "crude vanillin", namely a mixture essentially comprising vanillin, combined with heavy impurities known as "tar" and with small amounts of light impurities.

The problem is therefore that of recovering the product within specification, namely the aromatic aldehyde, present in the tar according to a process which both respects the integrity of the products to be separated and is economical and easy to implement in industrial devices, most particularly in those which operate continuously.

The present invention relates to a process for separating and recovering an aromatic aldehyde from a mixture comprising an aromatic aldehyde, light and heavy impurities and tar, characterized in that the liquid stream comprising said mixture is introduced into an evaporator, said mixture is vaporized such that, on the one hand, a gas stream comprising the aromatic aldehyde, the light impurities, the heavy impurities that can be vaporized at the selected evaporation temperature and pressure, and, on the other hand, a liquid stream essentially comprising the tar are separated, and in that the aromatic aldehyde is recovered from the separated gas stream.

According to one variant of the process of the invention, the separated gas stream essentially comprising the aromatic aldehyde obtained is recycled, in the gaseous state or after condensation, to a step upstream of this separation step.

In one preferred embodiment, the invention relates to a process for separating and recovering the aromatic aldehyde from a mixture comprising an aromatic aldehyde, light and heavy impurities and tar, characterized in that a prior concentration of the stream to be introduced into the evaporator is carried out.

Thus, before this separation step, the tar and the heavy impurities are concentrated by distillation, making it possible to recover the aromatic aldehyde and the light impurities at the distillation top and the tar and the heavy impurities at the distillation bottom.

According to one preferred variant of the process of the invention, the separated gas stream essentially comprising the aromatic aldehyde obtained, is recycled, in the gaseous state or after condensation, to the concentration step.

BRIEF DESCRIPTION

Figure 1:
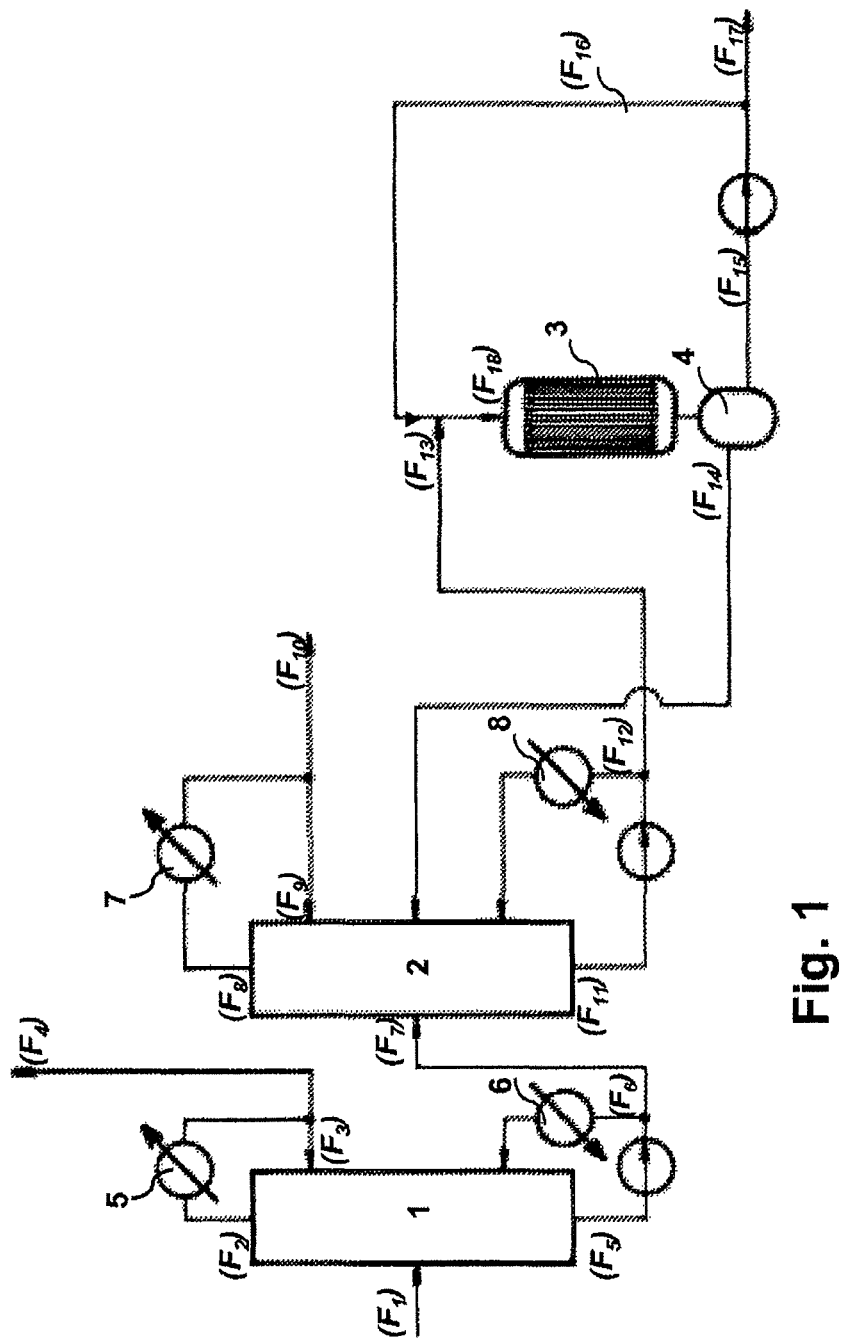
FIG. 1 is a diagrammatic representation of a preferred device for implementing the process according to the invention, comprising a column for distillation of the extraction solvent, a distillation column for concentrating the heavy compounds, and a falling-film evaporator coupled to this column.

In the present text, the term "light impurities" is intended to mean compounds of which the relative volatility is higher than that of the aromatic aldehyde, under the temperature and pressure conditions under consideration.

The light impurities are the starting phenolic compound, for example guaicol, guethol; the possible isomers of the aromatic aldehyde, such as o-vanillin and o-ethylvanillin; traces of the extraction solvent and possible impurities present in the solvent and the starting reactants.

The term "heavy compounds" and "heavy impurities" denotes compounds of which the relative volatility is lower than that of the aromatic aldehyde, under the temperature and pressure conditions under consideration.

The "heavy compounds" are essentially the tar which results from the preceding reaction steps and also, in smaller amounts, the heavy impurities of the process, for instance those which result from the oxidation of the formyl group to give a carboxyl group.

The starting mixture generally comprises from 55% to 94% by weight of an aromatic aldehyde, and from 6% to 45% by weight of light and heavy impurities, and tar.

The composition of the mixture is given by way of indication and the process of the invention is also suitable for mixtures that are richer in aromatic aldehyde (for example, a content of greater than 99% by weight of aromatic aldehyde) or richer in impurities (for example, a content greater than 60% by weight).

Typically, a crude vanillin leaving the distillation of the extraction solvent comprises from 55% to 94% by weight of vanillin, including the light impurities which represent from 1% to 10% of the weight of the vanillin, and the heavy compounds in a proportion of 5% to 60% by weight.

The process of the invention applies most particularly to vanillin and ethylvanillin, but it is also suitable for other aromatic aldehydes.

The term "aromatic aldehyde" is intended to mean a compound of substituted or unsubstituted benzaldehyde type, i.e., more specifically, a benzene nucleus comprising at least one formyl group.

It corresponds more particularly to the following formula:

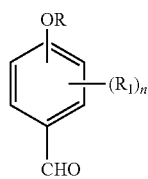

(I)

in said formula:
R represents a hydrogen atom or an alkyl group,
the $R_1$ groups, which may be identical or different, represent a hydrogen atom, a hydroxyl group, or an alkyl or alkoxy group,
n is a number from 0 to 4.

In the context of the invention, the term "alkyl" is intended to mean a linear or branched hydrocarbon-based chain containing from 1 to 12 carbon atoms, and preferably from 1 to 4 carbon atoms. Preferred examples of alkyl groups are methyl, ethyl, propyl and isopropyl groups.

The term "alkoxy" is intended to mean an alkyl-O— group in which the term alkyl has the meaning given above. Preferred examples of alkoxy groups are methoxy or ethoxy groups.

The aromatic aldehyde preferentially used in the process of the invention corresponds to formula (I) in which R represents a hydrogen atom or a methyl or ethyl group and $R_1$ represents a hydrogen atom or a methoxy or ethoxy group.

In formula (I), n is preferably equal to 1 or 2.

As more specific examples of aromatic aldehydes, mention may in particular be made of:
vanillin,
ethylvanillin (3-ethoxy-4-hydroxybenzaldehyde),
isovanillin (4-methoxy-3-hydroxybenzaldehyde),
o-vanillin (3-methoxy-2-hydroxybenzaldehyde),
protocatechualdehyde,
syringic aldehyde (3,5-dimethoxy-4-hydroxybenzaldehyde),
veratric aldehyde (3,4-dimethoxybenzaldehyde),
p-hydroxybenzaldehyde.

The process of the invention applies to a reaction medium comprising at least one aromatic aldehyde and various impurities, said aldehyde being extracted, after introduction of a formyl group, with an organic solvent.

Thus, at the end of the reaction, the aromatic aldehyde is extracted with an organic solvent or a mixture of organic solvents.

Use is made of an organic solvent which is inert with respect to the aromatic aldehyde.

As solvents that can be used, mention may in particular be made of aliphatic, cycloaliphatic or aromatic hydrocarbons, which are halogenated or nonhalogenated, alcohols, ketones and nitriles.

Mention is more particularly made, as aliphatic, cycloaliphatic or aromatic hydrocarbons, of heptane, cyclohexane, methylcyclohexane, benzene or toluene; as halogenated aliphatic, cycloaliphatic or aromatic hydrocarbons, of dichloromethane, trichloromethane, dichloroethane, chlorobenzene or dichlorobenzenes; as alcohols, of methanol, ethanol, propanol, isopropanol or butanol; as ketones, of acetone, methyl ethyl ketone, methyl isobutyl ketone or diisobutyl ketone; and as nitriles, of acetonitrile.

A mixture of said solvents may be used.

The extraction operation is carried out at a temperature which depends on the nature of the solvent.

The temperature is selected advantageously between 0° C. and 90° C., preferably between 20° C. and 80° C.

In order to isolate the aromatic aldehyde, firstly, the extraction solvent is eliminated by means of a distillation operation.

Throughout the process of the invention, the streams are kept to temperature by means of jacketed systems with circulation of a heat-transfer fluid or of steam.

As mentioned previously, the aromatic aldehyde present in the reaction medium is extracted using an organic solvent, examples of which are mentioned above.

At the end of the extraction operation, a liquid stream ($F_1$) comprising the aromatic aldehyde in solution in an extraction solvent is obtained. It most commonly comprises aromatic aldehyde at a concentration ranging between 5% and 70% by weight, from 20% to 94.8% by weight of an organic solvent and various light impurities and heavy compounds at a concentration ranging between 0.2% and 10% by weight.

The liquid stream ($F_1$) more preferably comprises from 10% to 60% by weight of aromatic aldehyde, from 35% to 89% by weight of an organic solvent and from 1% to 5% by weight of the various light impurities and of the heavy compounds.

A first step therefore consists in carrying out the separation of the aromatic aldehyde and of the extraction solvent by means of a distillation operation which results in the separation of said aldehyde.

More specifically, the distillation is designed so as to obtain:
- at the distillation bottom, a liquid phase ($F_5$) comprising the aromatic aldehyde accompanied by various light impurities and the heavy compounds,
- at the distillation top, a gas phase ($F_2$) comprising the extraction solvent and aromatic aldehyde at a low concentration enabling recycling of the solvent.

The term "low concentration" is intended to mean a concentration of aromatic aldehyde preferably of at most 100 ppm (0.01% by weight) in the organic solvent.

The distillation step is carried out at a temperature and a pressure which depend on the extraction solvent.

Generally, it is, for example for vanillin, at the distillation bottom, between 150° C. and 190° C., preferably between 160° C. and 180° C.

The distillation is preferably carried out under reduced pressure established at the column top.

The reduced pressure defined at the distillation bottom is generally between 20 and 100 mm of mercury, preferably between 20 and 40 mm of mercury.

According to one preferred variant of the process of the invention, this operation is carried out under an inert gas atmosphere, preferably under a nitrogen atmosphere.

The distillation operation is carried out in a conventional distillation apparatus, for example one or more distillation columns in series.

This distillation step aims to obtain, at the bottom, the aromatic aldehyde ($F_5$) devoid of the organic solvent.

Those skilled in the art are perfectly capable of selecting the means to be used according to the separation to be carried out.

The following will simply be recalled. The size (in particular the diameter) of the distillation columns depends on the circulating stream and on the internal pressure. Said columns will therefore be proportioned mainly according to the flow rate of mixture to be treated. The internal parameter represented by the number of theoretical stages is determined in particular by the purity of the starting compound and the purities of the products that must be obtained at the distillation top and bottom.

It will be specified that the column may be packed, without implied distinction, with plates or with stacked or woven packing, as is completely known to those skilled in the art.

The apparatus having been determined, those skilled in the art adjust the column operating parameters.

Thus, the distillation column may advantageously be, but not in a limiting manner, a column having the following specifications:
- number of theoretical stages: from 1 to 20, preferably from 2 to 10,
- degree of reflux R of between 0.05 and 15, preferably between 0.1 and 3.

The degree of reflux is defined by the ratio of the flow rate of material reinjected from the column top into the column and the flow rate actually leaving at the output of the column top.

In order to carry out the distillation, the provision of heat at the column bottom may be carried out in particular by means of a tube/shell heat exchanger heated with steam or with a heat-transfer fluid, by means of heating coils fed with steam or with a heat-transfer fluid or by any other equivalent device.

One preferred embodiment consists in heating the distillation bottom mixture in a heat exchanger by taking a bottom stream ($F_6$) which flows in a loop. More specifically, the stream ($F_5$) exits at the distillation bottom and a fraction ($F_6$) passes through a heat exchanger from bottom to top, and, on exiting the heat exchanger, is introduced laterally into the lower part of the distillation column.

Another embodiment consists in carrying out a forced circulation of the stream ($F_5$) in the heat exchanger by means of a pump.

The gas stream ($F_2$), at the column top, comprising predominantly the organic solvent and the aromatic aldehyde at a concentration preferably of at most 100 ppm, is condensed so as to recover a liquid stream, a fraction ($F_3$) of which is introduced laterally at the column top so as to provide the reflux in the column, and the other fraction ($F_4$) of which can be recycled to the extraction step.

The organic solvent is recovered from the stream ($F_2$) by condensation.

The gas phase ($F_2$) is cooled and is converted to liquid form by cooling by reducing the temperature of the stream ($F_2$), for example from 15° C. to 30° C., by passing it through one or more condensers, preferably one.

This operation is carried out by passage through a condenser which is a conventional apparatus, for example a tube heat exchanger fed with water or with a fluid (generally an oil, an alcohol, for example a glycol, or a water/glycol mixture, a brine) maintained at a temperature in the region of the chosen cooling temperature at the condenser output.

The number of condensers is selected according to the cooling capacities of the cooling liquids circulating in the condensers.

In the case of condensers in series, the gas phase at the output of the first condenser is introduced into the second condenser.

The organic solvent is recovered in liquid form at the base of the condenser(s).

A stream ($F_5$), namely a "crude aromatic aldehyde" which is a mixture essentially comprising aromatic aldehyde combined with heavy compounds, heavy impurities and "tar" and light impurities, is recovered at the distillation bottom.

By way of indication, it is specified that the stream ($F_5$) comprises between 89% and 98.5% by weight of aromatic aldehyde, between 1% and 5% by weight of light impurities, and heavy compounds in a proportion of from 0.5% to 6% by weight.

As mentioned above, one fraction ($F_6$) is recycled to the distillation column and the other fraction ($F_7$) is subjected to the subsequent operations, in particular concentration operations.

According to one preferred variant of the process of the invention, it has been found that the aromatic aldehyde obtained is of better quality as long as a step of concentrating the mixture to be treated is carried out before the step of separation by evaporation.

According to one preferred variant of the process of the invention, the stream ($F_7$) is concentrated in order to increase the concentration of the heavy compounds in the stream which is sent to the evaporator.

The stream ($F_7$) is concentrated according to a distillation operation.

More specifically, the distillation is designed so as to obtain:
- at the distillation bottom ($F_{11}$), the aromatic aldehyde accompanied by the heavy compounds, at the distillation top, a gas phase ($F_8$) essentially comprising the aromatic aldehyde, the light impurities and heavy impurities at a content of less than 100 ppm (0.01% by weight), preferably less than 50 ppm (0.005% by weight).

The distillation step is carried out at a distillation bottom temperature which is between 160° C. and 190° C., preferably between 165° C. and 185° C.

The distillation is preferably carried out under reduced pressure established at the column top. The reduced pressure defined at the distillation bottom is generally between 1 and 25 mm of mercury, preferably between 2 and 15 mm of mercury.

According to one preferred variant of the invention, this distillation operation is carried out under an inert gas atmosphere, preferably under a nitrogen atmosphere.

The distillation operation is carried out in a conventional distillation apparatus.

This step aims to obtain, at the bottom, a liquid stream ($F_{11}$) essentially comprising the aromatic aldehyde and also heavy impurities and tar.

Thus, the distillation column may be advantageously, but not in a limiting manner, a column having the following specifications:
  number of theoretical stages: from 1 to 30, preferably from 6 to 15,
  a degree of reflux R of between 0.05 and 15, preferably between 0.1 and 5.

In order to carry out the distillation, the provision of heat at the column bottom may be carried out in particular by means of a tube/shell heat exchanger heated with steam or with a heat-transfer fluid, by means of heating coils fed with steam or with a heat-transfer fluid or by any other equivalent device.

One preferred embodiment consists in heating the distillation bottom mixture in a heat exchanger by taking a bottom stream ($F_{12}$) which flows in a loop. More specifically, the stream ($F_{11}$) exits at the distillation bottom and a fraction ($F_{12}$) passes through a heat exchanger from bottom to top, and, on exiting the heat exchanger, is introduced laterally into the lower part of the distillation column.

Another embodiment consists in carrying out a forced circulation of the stream ($F_{11}$) in the heat exchanger by means of a pump.

The gas stream ($F_8$), at the column top, comprising predominantly the aromatic aldehyde and the light impurities, is condensed so as to recover a liquid stream, one fraction ($F_9$) of which is introduced laterally at the column top, so as to provide the reflux in the column, and the other fraction ($F_{10}$) of which can be treated in a subsequent step of purification of the aromatic aldehyde.

At the distillation top, the stream comprising essentially the aromatic aldehyde can be recovered from the stream ($F_8$) by condensation.

The gas phase ($F_8$) is cooled and is converted to liquid form by cooling by reducing its temperature, for example from 15° C. to 30° C., by passing it through one or more condensers, preferably one.

This operation is carried out by passage through a condenser which is a conventional apparatus, for example a tube heat exchanger fed with a heat-transfer fluid (generally an oil) maintained at a temperature in the region of the chosen cooling temperature.

The number of condensers is selected according to the cooling capacities of the cooling liquids circulating in the condensers.

In the case of condensers in series, the gas phase at the output of the first condenser is introduced into the second condenser.

The aromatic aldehyde ($F_{10}$) is recovered at the output of the condenser(s).

A stream ($F_{11}$), namely a mixture enriched in heavy impurities and tar, essentially comprising aromatic aldehyde combined with heavy impurities and tar, is recovered at the distillation bottom.

The concentration of the aromatic aldehyde in this stream ranges most commonly between 10% and 60% by weight, and that of the heavy compounds ranges between 40% and 90% by weight.

As mentioned above, one fraction ($F_{12}$) is recycled onto the distillation column and the other fraction ($F_{13}$) is subjected to an operation which makes it possible to recover the aromatic aldehyde present in the heavy compounds.

In accordance with the process of the invention, the aromatic aldehyde is separated and recovered from a mixture ($F_{13}$) having the same composition as the stream ($F_{11}$) comprising an aromatic aldehyde and heavy compounds, said process being characterized in that the liquid stream ($F_{13}$) is introduced into an evaporator, in that said mixture is vaporized such that, on the one hand, a gas stream ($F_{14}$) comprising the aromatic aldehyde, the heavy impurities that can be vaporized at the selected evaporation temperature and pressure and, on the other hand, a liquid stream ($F_{15}$) essentially comprising the heavy impurities and the tar are recovered, and in that the aromatic aldehyde is recovered from the separated gas stream ($F_{14}$).

According to one variant of the process of the invention, the gas stream obtained ($F_{14}$) is recycled, in the gaseous state or after condensation, to a step upstream of the separation step.

In one preferred variant of the process of the invention, the separated gas stream ($F_{14}$) is recycled, in the gaseous state or after condensation, to the concentration step.

The process parameters vary according to the type of evaporator used in the process of the invention.

Various types of evaporators can be selected, thus resulting in several process variants.

Several types of evaporators are suitable for implementing the process of the invention, in particular falling-film evaporators, wiped film evaporators, short-path evaporators with an internal condenser, horizontal wiped evaporators, or any variant of these devices.

According to one preferred embodiment of the process of the invention, the separation is carried out in an evaporator maintained under an inert atmosphere, preferably under a nitrogen atmosphere.

Thus, in accordance with a first variant of the process of the invention, the separation is carried out in a falling-film evaporator.

The term "falling-film evaporator" is intended to mean a device constituted of a generally cylindrical chamber comprising a bundle of vertical tubes, said tubes being heated externally, for example, by circulation of steam in said chamber.

The mixture ($F_{13}$), comprising an aromatic aldehyde, heavy impurities and tar, is fed via the upper part and comes across a distribution system, for example with an overflow, allowing good distribution of the liquid at the top of the tubes in order to constitute a liquid film of fine thickness, generally less than 1 mm, preferably between 0.3 and 0.5 mm.

Said mixtures flows by gravity along the internal surface of the tubes and the fractions that can be vaporized (including the aromatic aldehyde) are evaporated off as they are conveyed along the tubes and the liquid phase, essentially the heavy compounds, reaching the base of the tubes is then separated from the fractions that can be vaporized.

The mixture ($F_{13}$) is introduced into the falling-film evaporator, passes through it from top to bottom and, on exiting, passes through a separation chamber which separates the two liquid and gas streams. The separator can be a cylindrical device comprising no internal material, i.e. neither plates nor packing.

A gas stream ($F_{14}$) essentially comprising the aromatic aldehyde and heavy impurities that can be vaporized is recovered at the top of the separation chamber and a liquid stream ($F_{15}$) essentially comprising heavy compounds, heavy impurities and tar is recovered at the bottom of the separation chamber.

According to the preferred variant of the process of the invention, the gas stream ($F_{14}$) is recycled upstream of this step of separation by evaporation, and more particularly to the concentration step.

Generally, this stream is introduced laterally onto the concentrating column, it being possible for this stream to be optionally condensed in order to be introduced in liquid form by means of a pump.

In the gas stream ($F_{14}$), the concentration of aromatic aldehyde most commonly ranges between 20% and 75% by weight, preferably between 25% and 60% by weight.

The liquid stream ($F_{15}$) is therefore separated from the gas stream ($F_{14}$), and one fraction ($F_{16}$) of the stream ($F_{15}$) is recycled to the evaporator feed and the other fraction ($F_{17}$) is eliminated and its potential can subsequently be exploited.

In the output liquid stream ($F_{15}$), the concentration of aromatic aldehyde most commonly ranges between 1% and 20% by weight, preferably between 1% and 10%.

According to one variant of the process of the invention, a fraction of the heavy compounds ($F_{16}$) is recycled or recirculated in order to maintain a liquid film with no dry zone over the entire height of the tubes, thereby improving the separation and recovery yield.

The separated liquid stream comprising the tar is generally recycled with a recycling rate of from 50% to 75%.

In one mode of operation of the evaporator with recycling of the stream ($F_{16}$), the feed ($F_{18}$) is then composed of the mixture of the streams ($F_{13}$) and ($F_{16}$).

In the case of the recycling of a liquid stream ($F_{16}$), the ($F_{16}$)/($F_{13}$) recycling mass ratios are between 1 and 10.

The residence times in the evaporator are short: they are between 30 seconds and 10 minutes.

The step of separating the aromatic aldehyde from the heavy compounds is carried out in the evaporator, by vaporization of the aromatic aldehyde and of the heavy impurities present that can be vaporized.

The vaporization rate expressed by the weight ratio between the gas stream and the feed stream is between 5% and 75% by weight, preferably between 5% and 50% by weight.

The evaporation temperatures (average temperature in the film) are between 170° C. and 200° C. with a temperature gradient between the top and the bottom of the evaporator of between 10° C. and 20° C. and a pressure established at the top of the evaporator of between 1 and 20 mm of mercury.

The reduced pressure is established on the device by means of a vacuum circuit connected at the top of the evaporator.

In this step of separation by evaporation, the recovery yield for the aromatic aldehyde present in the heavy compounds, expressed by the weight ratio of the aromatic aldehyde vaporized ($F_{14}$) to the aromatic aldehyde contained in the feed stream ($F_{13}$) is about 80% to 90%.

The present invention also relates to a piece of equipment for implementing the process according to the invention.

This device comprises a distillation column for concentrating the heavy compounds and a falling-film evaporator for separating and recovering the aromatic aldehyde from a mixture comprising, in addition, tar.

In one embodiment, it also comprises at least one column for distillation of the extraction solvent.

The invention will be understood more clearly on reading the description of FIG. 1, appended to the present application.

FIG. 1 is a diagrammatic representation of a preferred device for implementing the process according to the invention, comprising column 1 for distillation of the extraction solvent, distillation column 2 for concentrating the heavy compounds and the falling-film evaporator 3 coupled to this column.

In FIG. 1, the stream ($F_1$) coming from the extraction step and comprising the reaction products, including the heavy compounds, is introduced into distillation column 1, enabling, by distillation, the separation of the extraction solvent from the aromatic aldehyde.

At the top of distillation column 1, after condensation of the vapor stream ($F_2$) on the condenser 5, an extraction solvent stream ($F_4$) is recovered and can be recycled to the extraction step; a part of the condensed stream ($F_3$) is sent back laterally to the top of column 1 and constitutes the reflux of column 1.

The gas stream ($F_2$) is cooled by reducing its temperature, for example from 15° C. to 30° C., by passing it through one or more condensers 5, preferably one.

At the bottom of distillation column 1, the overall stream ($F_5$) is predominantly recirculated to the column bottom while passing over the heat exchanger 6; the stream ($F_7$) will feed distillation column 2 for concentrating the heavy compounds.

At the top of column 2, after condensation of the vapor stream ($F_8$) on the condenser 7, a stream ($F_{10}$) of the aromatic aldehyde and the light impurities is recovered; a part of the condensed stream ($F_9$) is sent back laterally to the top of column 2 and constitutes the reflux of column 2.

The stream ($F_{10}$) feeds the device(s) for final purification of the aromatic aldehyde.

The gas stream ($F_8$) is cooled by reducing its temperature, for example from 15° C. to 30° C., by passing it through one or more condensers 7, preferably one.

At the bottom of distillation column 2, the overall stream ($F_{11}$) is predominantly recirculated ($F_{12}$) to the column bottom while passing over the heat exchanger 8; the stream ($F_{13}$) will feed the falling-film evaporator 3.

The stream ($F_{13}$) is introduced into the upper part of the evaporator 3.

The stream leaving the evaporator 3 passes through a separation chamber 4 for separating a liquid stream ($F_{15}$) from a gas stream ($F_{14}$).

The gas stream leaving the separation chamber 4 ($F_{14}$) is sent back laterally to the concentrating column 2, preferably at the bottom of the column.

According to one variant of the process of the invention, it is possible to send the stream ($F_{14}$) back to the column in liquid form by means of a pump, after passage through a condenser. The pump and the condenser are not represented in FIG. 1.

A part of the liquid stream ($F_{15}$) derived from the separation chamber 4, namely the stream ($F_{16}$), is recycled to the feed of the evaporator 3 and, together with the feed stream ($F_{13}$), constitutes the overall feed stream ($F_{18}$) of the evaporator 3.

The other part of the liquid stream ($F_{17}$) depleted of aromatic aldehyde essentially comprises the tar and the heavy impurities; this stream is eliminated and its potential can be subsequently exploited.

Thus, in accordance with a second variant of the process of the invention, the separation is carried out in a wiped-film evaporator.

The term "wiped-film evaporator" is intended to mean a device constituted of a generally cylindrical or cylindro-conical chamber which has an external jacket fitted with an inlet and an outlet for circulation of a heat-transfer fluid which allows the chamber to be heated.

In this type of device, the film is formed on the internal wall of the chamber by plating using mechanical means specified hereinafter.

The chamber is equipped, centrally, with an axial rotor on which the mechanical means which allow the formation of the film on the wall are mounted. The rotors may be rotors equipped with fixed blades: lobe rotors with three or four blades made of flexible or rigid materials, distributed over the entire height of the rotor, or else rotors equipped with moving blades, vanes, wiper brushes or guided wipers. In this case, the rotor is constituted of a succession of vanes articulated on a pivot and mounted on a shaft or axle by means of radial supports. Other rotors are equipped with moving rollers mounted on secondary axles and said rollers are pushed against the wall by centrifugation.

The rotational speed of the rotor, which depends on the size of the device, is readily determined by those skilled in the art. By way of indication, it is specified that the peripheral speed can range between 0.3 and 3 m/s for moving-blade rotors; 5 and 15 m/s for fixed-blade rotors.

The various spindles may be made of various materials, metals, for example steel, alloy steel (stainless steel) or aluminum, or polymeric materials, for example polytetrafluoroethylene PTFE or glass materials (enamel); metals coated with polymeric materials.

The mixture ($F_{13}$), comprising an aromatic aldehyde, heavy impurities and tar, is fed via the upper part and is centrifuged onto the wall by means of a distributor, for example a disk rigidly connected to the rotor. The liquid is distributed over the wall and forms a liquid film of fine thickness, generally between 0.25 and 1 mm, plated by the mechanical means specified above.

Said mixture descends by gravity along the internal surface of the wall and the fractions that can be vaporized (including the aromatic aldehyde) are evaporated off as they pass along the wall, and the liquid phase, essentially the heavy compounds, reaching the base of the chamber is recovered.

At the top of the chamber, a gas stream ($F_{14}$) essentially comprising the aromatic aldehyde and the heavy impurities that can be vaporized is recovered, and at the bottom of the chamber, a liquid stream ($F_{19}$) essentially comprising the heavy compounds, heavy impurities and tar is recovered.

In order to keep the stream ($F_{14}$) entirely in gas form, it is desirable to envision a droplet demisting device (or droplet separator) located in the upper part of the chamber in the gas stream ($F_{14}$) evacuation zone.

On leaving, the gas stream ($F_{14}$) is recycled upstream of this step of separation by evaporation, preferably to the concentration step; this stream can be optionally condensed in order to be introduced in liquid form by means of a pump.

In the gas stream ($F_{14}$) the concentration of aromatic aldehyde ranges most commonly between 25% and 75% by weight.

The liquid stream ($F_{19}$) is collected at the base in any relay storage device, said device being heated in order to keep the stream liquid.

The liquid stream ($F_{19}$) separated from the gas stream ($F_{14}$) is fractionated: one fraction of the stream ($F_{20}$) is recycled to the evaporator feed and the other fraction ($F_{21}$) is eliminated and its potential can be subsequently exploited.

In the output liquid stream ($F_{19}$), the concentration of aromatic aldehyde ranges most commonly between 1% and 20% by weight.

According to one variant of the process of the invention, a fraction of the heavy compounds ($F_{20}$) is recycled or recirculated. However, the recycling is not imperative since the film is formed mechanically.

The separated liquid stream comprising the tar can be recycled with a recycling rate of 0 to 50%.

In one mode of operation of the evaporator with recycling of the stream ($F_{20}$), the feed ($F_{18}$) is then composed of the mixture of the streams ($F_{13}$) and ($F_{20}$).

In the case of the recycling of a liquid stream ($F_{20}$), the ($F_{20}$)/($F_{13}$) recycling mass ratios are between 0.1 and 10, preferably 0.1 and 2.

The residence times in the evaporator are short. They are between 30 seconds and 10 minutes.

The step of separating the aromatic aldehyde from the heavy compounds is carried out in the evaporator, by vaporization of the aromatic aldehyde and of the heavy impurities present that can be vaporized.

The vaporization rate, expressed by the weight ratio between the gas stream and the feed stream, is between 20% and 90%, preferably between 40% and 80%.

The evaporation temperatures (average temperature in the film) are between 170° C. and 200° C. with a temperature gradient between 10° C. and 20° C. and a pressure established at the top of the evaporator of between 1 and 20 mm of mercury.

The reduced pressure is established on the device by means of a vacuum circuit generally connected at the bottom or at the output of the evaporator.

In this step of separation by evaporation, the aromatic aldehyde recovery yield, expressed by the weight ratio of the aromatic aldehyde vaporized ($F_{14}$) to the aromatic aldehyde contained in the feed stream ($F_{13}$) ranges most commonly between 85% and 99%, preferably between 90% and 99%.

The present invention also relates to a piece of equipment for implementing the process according to the invention.

This device comprises a distillation column for concentrating the heavy compounds and a wiped-film evaporator for separating and recovering the aromatic aldehyde from a mixture comprising, in addition, tar.

In one embodiment, it also comprises at least one column for distillation of the extraction solvent.

Figure 2:
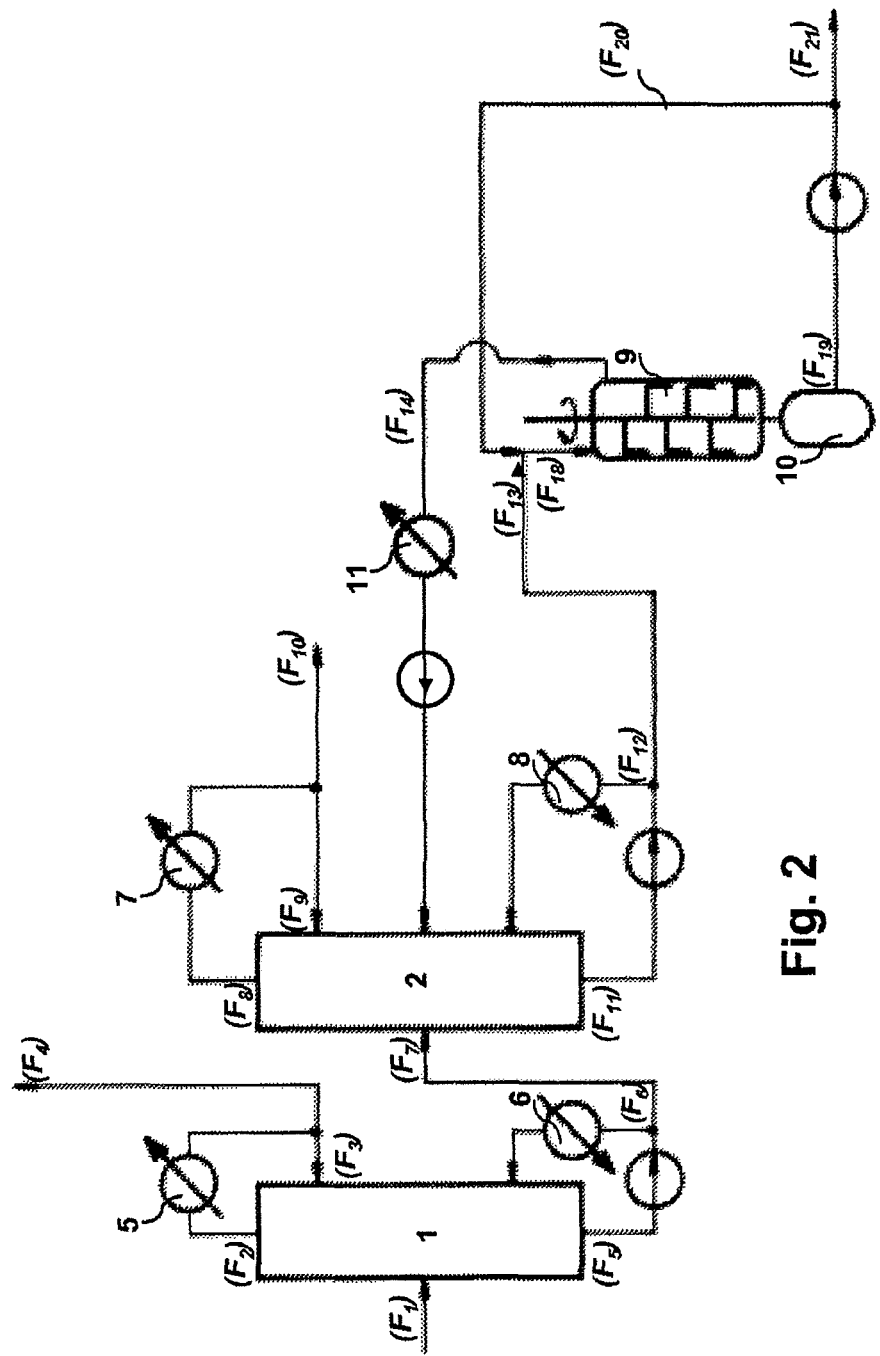
FIG. 2 is a diagrammatic representation of a preferred device for implementing the process according to the invention, comprising a column for distillation of the extraction solvent, a distillation column for concentrating the heavy compounds, and a wiped-film evaporator coupled to this column.

FIG. 2 is a diagrammatic representation of a preferred device for implementing the process according to the invention, comprising column 1 for distillation of the extraction solvent, distillation column 2 for concentrating the heavy compounds and the wiped-film evaporator 9 coupled to this column.

In FIG. 2, the stream ($F_{13}$) obtained, as mentioned for FIG. 1, is introduced into the upper part of the evaporator 9.

The liquid stream ($F_{19}$) is recovered at the bottom of the evaporator 9.

The gas stream ($F_{14}$) is recovered at the top of the evaporator 9 and sent back laterally to the concentrating column 2, preferably at the bottom of the column.

According to one preferred variant of the process of the invention, it is possible to send the stream ($F_{14}$) back to column 2 in liquid form by means of a pump, after passage through a condenser 11.

A part of the liquid stream ($F_{19}$) recovered at the bottom of the evaporator in the device 10 is recycled to the feed of the evaporator 9 and, together with the feed stream ($F_{13}$), constitutes the overall feed stream ($F_{18}$) of the evaporator 9.

The other part of the liquid stream ($F_{21}$) depleted of aromatic aldehyde essentially comprises the tar and the heavy impurities; this stream is eliminated and its potential can be subsequently exploited.

Thus, in accordance with a third variant of the process of the invention, the separation is carried out in a short-path evaporator with an internal condenser.

The expression "short-path evaporator with an internal condenser" is intended to mean a device constituted of a generally cylindrical chamber which has an external jacket fitted with an inlet and an outlet for the circulation of a heat-transfer fluid which heats the chamber.

In this type of device, the film is formed on the internal wall of the chamber by plating using mechanical means as specified hereinafter.

The chamber is equipped with an axial rotor in the upper part of the chamber and, below, a central internal condenser.

Secondary axles are installed on a device rigidly connected to the central rotor, said axles being vertical shafts on which sliding rollers are mounted.

The various rollers may be made of various materials, metals, for example steel, alloy steel (stainless steel) or aluminum, or polymeric materials, for example polytetrafluoroethylene PTFE, or metals coated with polymeric materials.

The film is formed on the wall by centrifugation and by the rollers being pushed onto the wall by rotation of the rotor.

The rotational speed of the rotor, which depends on the size of the device, is readily determined by those skilled in the art. By way of indication, it is specified that the peripheral speed can range between 0.3 and 3 m/s.

The condenser placed at the center of the chamber makes it possible to condense the vapors right inside the evaporation device. It may be a tube exchanger, for example coils or bundles of tubes.

The mixture ($F_{13}$), comprising an aromatic aldehyde, heavy impurities and tar, is fed via the upper part and is centrifuged onto the wall by means of a distributor, for example a disk rigidly connected to the rotor. The liquid is distributed over the wall and forms a liquid film of fine thickness, generally between 0.25 and 1 mm, plated by the mechanical means specified above.

Said mixture flows by gravity along the internal surface of the wall and the fractions that can be vaporized (including the aromatic aldehyde) are evaporated off and immediately condensed by means of the central condenser, and the condensed fraction ($F_{14}$) flows by gravity over the walls of the internal condenser and the condensed vapors are collected at the base of the device in an internal collector.

A liquid phase ($F_{14}$) is recovered in said collector, said phase essentially comprising the aromatic aldehyde and the heavy impurities that can be vaporized, and a liquid stream ($F_{15}$) essentially comprising the heavy compounds, heavy impurities and tar is recovered at the bottom of the chamber.

According to one preferred variant of the process of the invention, the liquid stream ($F_{14}$) is, on leaving, recycled upstream of this step of separation by evaporation, more particularly to the concentration step: this stream is introduced by means of a pump.

In the liquid stream ($F_{14}$), the concentration of aromatic aldehyde ranges most commonly between 25% and 75% by weight.

The nonvaporized liquid stream ($F_{15}$) is collected at the base in any relay storage device, said device being heated in order to keep the stream liquid.

The potential of the liquid stream ($F_{15}$) can be subsequently exploited.

In the output liquid stream ($F_{15}$), the concentration of aromatic aldehyde ranges most commonly between 1% and 15% by weight.

The residence times in the evaporator are short. They are between 30 seconds and 10 minutes.

The step of separating the aromatic aldehyde from the heavy compounds is carried out in the evaporator, by vaporization of the aromatic aldehyde and of the heavy impurities present that can be vaporized.

The vaporization rate, expressed by the weight ratio between the gas stream and the feed stream, is between 10% and 95%, preferably between 15% and 90%.

The evaporation temperatures (average temperature in the film) are between 170° C. and 200° C. with a temperature gradient between the top and the bottom of the evaporator of between 10° C. and 20° C. and a pressure established at the top of the evaporator of between 0.01 and 20 mm of mercury, preferably between 0.1 and 10 mm of mercury.

The reduced pressure is established on the device by means of a vacuum circuit generally connected at the bottom or at the output of the evaporator.

In this step of separation by evaporation, the aromatic aldehyde recovery yield, expressed by the weight ratio of the aromatic aldehyde vaporized ($F_{14}$) to the aromatic aldehyde contained in the feed stream ($F_{13}$), ranges most commonly between 85% and 99%, preferably between 90% and 99%.

The present invention also relates to a piece of equipment for implementing the process according to the invention.

This device comprises a distillation column for concentrating the heavy compounds and a short-path evaporator with an internal condenser for separating and recovering the aromatic aldehyde from a mixture comprising, in addition, tar.

In one embodiment, it also comprises at least one column for distillation of the extraction solvent.

Figure 3:
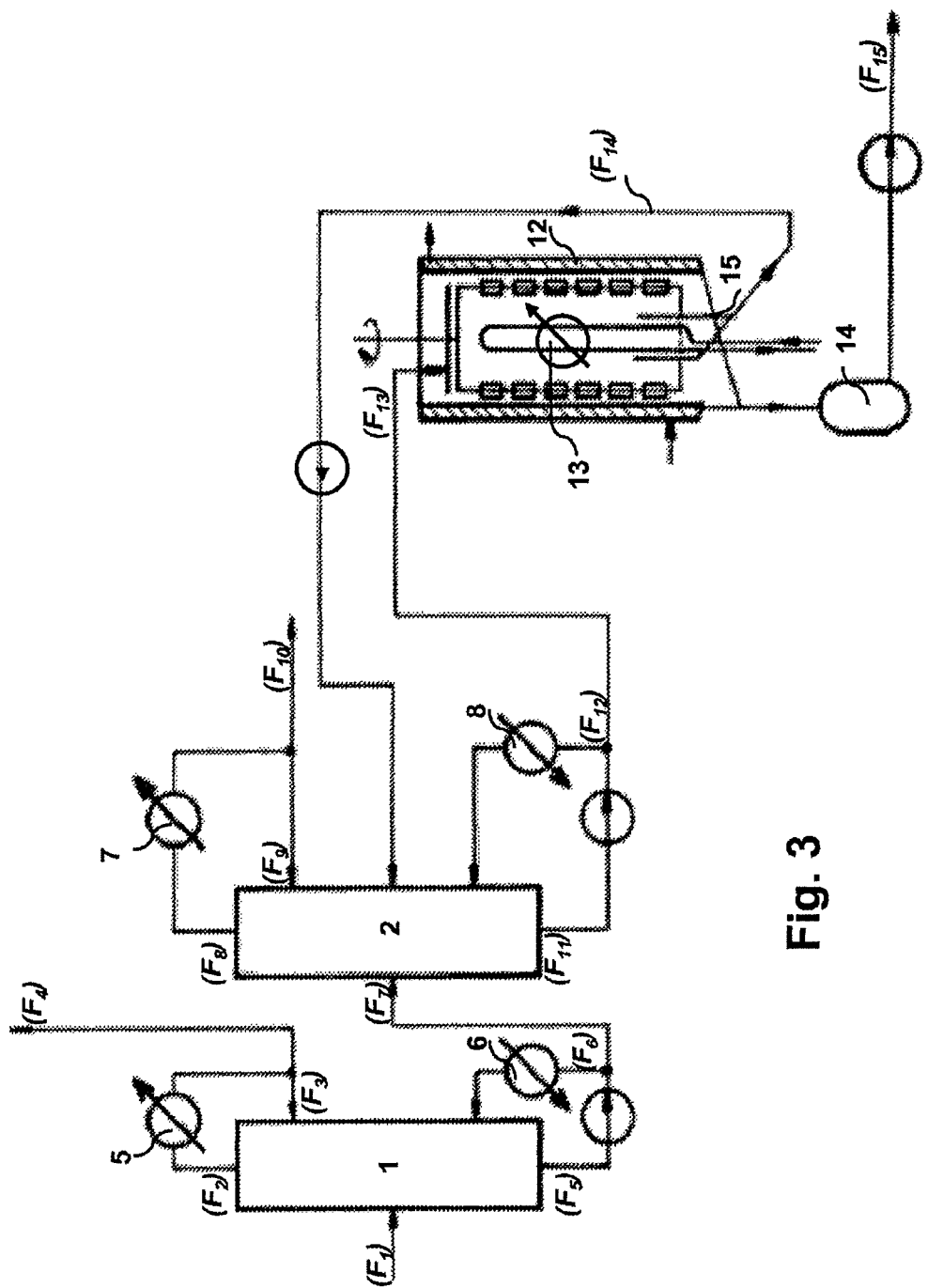
FIG. 3 is a diagrammatic representation of a preferred device for implementing the process according to the invention, comprising a column for distillation of the extraction solvent, a distillation column for concentrating the heavy compounds, and a short-path evaporator with an internal condenser, coupled to this column.

FIG. 3 is a diagrammatic representation of a preferred device for implementing the process according to the invention, comprising column 1 for distillation of the extraction solvent, distillation column 2 for concentrating the heavy compounds and the short-path evaporator 12 with an internal condenser 13, coupled to this column.

In FIG. 3, the stream ($F_{13}$) obtained as mentioned for FIG. 1 is introduced in the upper part of the evaporator 12.

The liquid stream ($F_{15}$) is recovered at the bottom of the evaporator 12.

The gas stream ($F_{14}$) condensed inside the evaporator on the condenser 13 is recovered at the bottom of the evaporator 12 in the condensate collector 15 and sent back laterally to the concentrating column 2, preferably at the bottom of the column. The stream ($F_{14}$) which is liquid is sent back by means of a pump.

The liquid stream ($F_{15}$) is collected in a storage device 14.

It essentially comprises the tar and the heavy impurities which are evacuated and the potential of which can be subsequently exploited.

Thus, in accordance with a fourth variant of the process of the invention, the separation is carried out in a horizontal wiped evaporator.

The expression "horizontal wiped-film evaporator" is intended to mean a device constituted of a generally cylindrical chamber placed horizontally, which has an external jacket fitted with an inlet and an outlet for circulation of a heat-transfer fluid which heats the chamber.

In this type of device, the film is formed on the internal wall of the chamber by plating using mechanical means specified hereinafter.

The chamber is equipped centrally with a horizontal axial rotor, optionally heated by internal circulation of a heat-transfer fluid, the mechanical means which allow the formation of the film on the wall being mounted on said rotor. The rotor may be a rotor equipped with a succession of fixed vanes mounted at the periphery of the rotor. The arrangement of the vanes on the rotor is such that it causes the film to advance toward the output end of the chamber, opposite the feed end; worm screw movement profile. It is possible, according to the device, to envision profiled counter-blade systems on the wall which allow, by means of an interaction with the vanes, automatic cleaning of the internal surfaces of the evaporator and of the rotor.

It is also possible to have, in one chamber, two rotors in parallel which rotate in the same direction or in opposite directions.

The various spindles are generally made of metals, most commonly of steel or an alloy steel (stainless steel).

The mixture ($F_{13}$), comprising the aromatic aldehyde, the heavy impurities and the tar, is fed at one end of the chamber of the evaporator and on the top thereof. The liquid is distributed over the wall and the thickness of the liquid film is adjusted by means of the mechanical play between the fixed blades of the rotor and the internal wall of the chamber equipped with counter-blades.

The thickness of the film generally ranges between 1 and 3 mm. The device enables a flow, preferably a piston flow, of the liquid in the direction of the output.

Said mixture advances transversely in the chamber and the fractions that can be vaporized ($F_{14}$), essentially comprising the aromatic aldehyde and the heavy impurities that can be vaporized, are evaporated off and collected by an output pipe located on the top of the chamber and are then sent to a condenser.

The evacuation pipe for the fractions that can be vaporized can be equipped with a filter kept at a temperature above that of the vapors.

The liquid phase ($F_{15}$) essentially comprising the heavy compounds, heavy impurities and tar is recovered at the end opposite the feed, in a relay storage device.

The gas stream ($F_{14}$) is, on leaving, recycled upstream of this step of separation by evaporation.

According to one preferred variant of the process of the invention, it is recycled to the concentration step: this stream is condensed in order to be introduced in liquid form by means of a pump.

In the gas stream ($F_{14}$), the concentration of aromatic aldehyde ranges most commonly between 25% and 75% by weight.

The liquid stream ($F_{15}$) is collected at the base in any relay storage device, said device being heated in order to keep the stream liquid.

In the output liquid stream ($F_{15}$), the concentration of aromatic aldehyde ranges most commonly between 1% and 15% by weight; this stream is eliminated and its potential can be subsequently exploited.

The residence times in the evaporator are between 30 seconds and 10 minutes.

The step for separating the aromatic aldehyde from the heavy compounds is carried out in the evaporator, by vaporization of the aromatic aldehyde and of the heavy impurities present that can be vaporized.

The vaporization rate, expressed by the weight ratio between the gas stream and the feed stream, is between 10% and 90%, preferably between 15% and 90%.

The evaporation temperatures (average temperature in the film) are between 170° C. and 200° C. with a temperature gradient between the input and the output of the evaporator of between 10° C. and 20° C. and a pressure established at the top of the evaporator of between 2 and 20 mm of mercury.

The reduced pressure is established on the device by means of a vacuum circuit generally connected at the top of the evaporator.

In this step of separation by evaporation, the aromatic aldehyde recovery yield, expressed by the weight ratio of the aromatic aldehyde vaporized ($F_{14}$) to the aromatic aldehyde contained in the feed stream ($F_{13}$), ranges most commonly between 90% and 99%, preferably between 95% and 99%.

The present invention also relates to a piece of equipment for implementing the process according to the invention.

This device comprises a distillation column for concentrating the heavy compounds and a horizontal wiped-film evaporator for separating and recovering the aromatic aldehyde from a mixture comprising, in addition, tar.

In one preferred embodiment, it also comprises a column for distillation of the extraction solvent.

Figure 4:
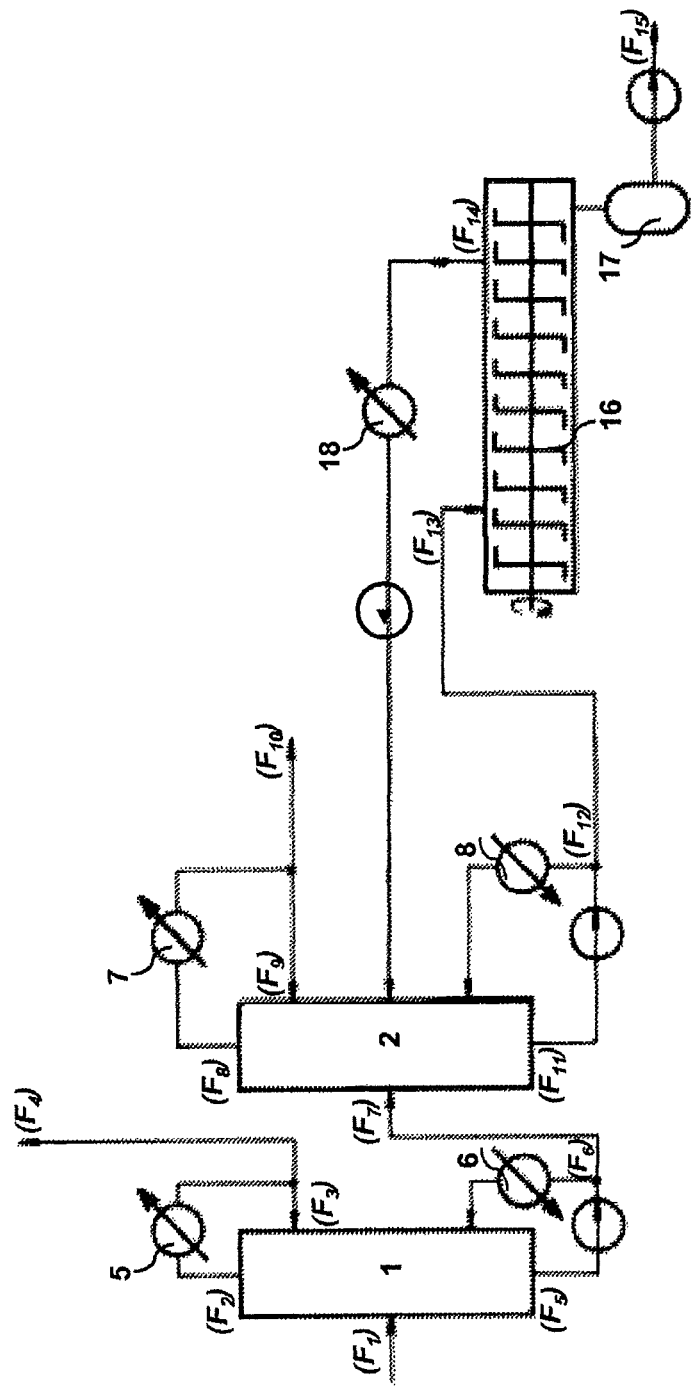
FIG. 4 is a diagrammatic representation of a preferred device for implementing the process according to the invention, comprising a column for distillation of the extraction solvent, a distillation column for concentrating the heavy compounds, and a horizontal wiped-film evaporator 16 coupled to this column.

FIG. 4 is a diagrammatic representation of a preferred device for implementing the process according to the invention, comprising column 1 for distillation of the extraction solvent, distillation column 2 for concentrating the heavy compounds and the horizontal wiped-film evaporator 16 coupled to this column.

In FIG. 4, the stream ($F_{13}$) obtained as mentioned for FIG. 1 is introduced at the top part of the evaporator 16 and at one end thereof.

The liquid stream ($F_{15}$) is recovered at the other end of the evaporator 16.

The gas stream ($F_{14}$) is recovered on the top of the evaporator 16 and sent back laterally to the concentrating column 2, preferably at the bottom of the column, after condensation on the condenser 18 and transfer by means of a pump, for example a positive-displacement pump.

The liquid stream ($F_{15}$) which essentially comprises the tar and the heavy impurities is collected in a relay storage device 17; this stream is eliminated and its potential can be subsequently exploited.

As described previously, the separation according to the invention can be carried out in a falling-film evaporator, a wiped-film evaporator, a short-path evaporator or a horizontal wiped-film evaporator. The invention includes the case where several evaporators can be mounted in series. Mention may in particular be made of the use of a horizontal evaporator coupled to the output of another type of evaporator as mentioned above.

In accordance with the process of the invention, the separation of the aromatic aldehyde lies within a continuous process with continuous introduction of the streams and continuous recovery of the streams.

However, the invention does not exclude a batchwise embodiment.

The present invention allows the heavy compounds to be eliminated and the separated streams to be continuously recycled in an industrial apparatus.

The process of the invention makes it possible to recover the aromatic aldehyde present in the heavy compounds with sufficiently short residence times and temperature and pressure conditions which make it possible to respect the integrity of the product to be separated, while at the same time being simple to implement.

Exemplary embodiments of the invention obtained on a pilot apparatus operating in continuous mode are given hereinafter.

The examples are given by way of illustration and are not limiting in nature.

In the examples, the analyses of the streams (including the vanillin) are carried out by high performance liquid chromatography.

As previously mentioned in the description, all the equipment is maintained under a nitrogen atmosphere.

EXAMPLE 1

In this example, an illustration is given of the process which makes it possible to recover the vanillin present in tar, using a falling-film evaporator as illustrated in FIG. 1, intended for treating tar obtained after liquid/liquid extraction of a reaction mixture resulting from the synthesis of vanillin (VA).

The stream ($F_1$) which feeds column 1 has a vanillin content of 0.4000 kg/kg, a light impurity content of 0.0144 kg/kg and a heavy impurity content of 0.0084 kg/kg.

The stream ($F_1$) is introduced into column 1 with a feed flow rate of 211.48 kg/h.

At the top of column 1, a liquid stream ($F_4$) is recovered, after condensation, at a rate of 122.07 kg/h, said stream no longer containing vanillin.

At the bottom of column 1, a liquid stream ($F_5$) is withdrawn at a rate of 600 kg/h, said stream comprising 0.9461 kg of vanillin per kg of stream ($F_5$).

The stream ($F_7$) is then introduced into distillation column 2 with a feed flow rate of 89.41 kg/h. Its vanillin content is 0.9461 kg/kg.

Column 2 which is used has the following characteristics and operating conditions:

TABLE (I)

| Column 2 | |
|---|---|
| Diameter (mm) | 200 |
| Height (mm) | 2500 |
| Total NTS (number of theoretical stages) reboiler included | 11 |
| NTS (number of theoretical stages) below the feed | 9 |
| Pressure at top of column 2 (mmHg) | 8 |
| Pressure at bottom of column 2 (mmHg) | 16 |
| Temperature at top of column 2 (° C.) | 145 |
| Temperature at bottom of column 2 (° C.) | 181 |
| Load factor $(kg/m^3)^{0.5} \times m \cdot s^{-1}$ | 4.3 |
| Mean relative volatility (VA/heavy compounds) | 8.0 |
| Reflux top of column 2: ($F_9$) after condenser 7 (kg/h) | 21.9 |
| Recycling bottom of column 2: ($F_{12}$) on exchanger 8 (kg/h) | 550 |
| Heat load to the boiler (kcal/h) | 13 050 |

At the top of column 2, a gas stream ($F_8$), which after condensation becomes the stream ($F_{10}$), is recovered at a rate of 87.5 kg/h and contains vanillin at a content of 0.9645 kg/kg.

At the bottom of column 2, a liquid stream ($F_{11}$) is withdrawn at a rate of 554.2 kg/h, said stream comprising 0.2965 kg of vanillin per kg of stream ($F_{11}$).

A fraction ($F_{13}$) of the stream ($F_{11}$) feeds the falling-film evaporator 3, the other fraction ($F_{12}$) being reintroduced laterally into distillation column 2.

The characteristics and the operating conditions of the evaporator 3 are collated in table (II):

TABLE (II)

| Falling-film evaporator 3 | |
|---|---|
| Number of tubes | 10 |
| Diameter of a tube (mm) | 10 |
| Tube thickness (mm) | 2 |
| Height (mm) | 800 |
| Total exchange surface ($m^2$) | 0.251 |
| Evaporator pressure (mmHg) | 14 |
| Heat-transfer fluid temperature (° C.) | 195 |
| Average film temperature (° C.) | 185 |
| Average feed viscosity (cPo) | 150 |
| Overall heat transfer coefficient ($kcal/hm^{2\circ}$ C.) | 180 |
| Heat load of the falling-film evaporator (kcal/h) | 454 |
| Mean relative volatility VA/heavy compounds (mmHg/mmHg) | 5.6 |
| Feed from column 2: ($F_{13}$) (kg/h) | 4.198 |
| VA content in ($F_{13}$) (kg/kg) | 0.297 |
| Total feed ($F_{18}$) (kg/h) | 29.50 |
| VA content in ($F_{18}$) (kg/kg) | 0.1317 |
| Vaporization and recycling to column 2: ($F_{14}$) (kg/h) | 2.288 |
| VA content in ($F_{14}$) (kg/kg) | 0.456 |
| Liquid at bottom of evaporator: ($F_{15}$) (kg/h) | 27.23 |
| VA content in ($F_{15}$) (kg/kg) | 0.104 |
| Recycling to the feed of the falling film: ($F_{16}$) (kg/h) | 25.32 |
| VA content in ($F_{16}$) (kg/kg) | 0.104 |
| Tar extracted: ($F_{17}$) (kg/h) | 1.909 |
| VA content in ($F_{17}$) (kg/kg) | 0.104 |
| VA losses in ($F_{17}$) (kg/h) | 0.199 |
| Falling-film evaporator vaporization rate (% by mass) | 7.7 |
| Falling-film evaporator VA recovery yield (% by mass) | 83.8 |

EXAMPLE 2

This example provides an illustration of the process which makes it possible to recover the vanillin present in tar using a falling-film evaporator as illustrated in FIG. 1 intended for treating tar obtained after liquid/liquid extraction of a reaction mixture resulting from the synthesis of vanillin (VA).

The stream ($F_1$) which feeds column 1 has a vanillin content of 0.6000 kg/kg, a light impurity content of 0.0215 kg/kg and a heavy impurity content of 0.0127 kg/kg.

The stream ($F_1$) is introduced into column 1 with a feed flow rate of 78.84 kg/h.

At the top of column 1, a liquid stream ($F_4$) is recovered, after condensation, at a rate of 28.80 kg/h, said stream no longer containing vanillin.

At the bottom of column 1, a liquid stream ($F_5$) is withdrawn at a rate of 500 kg/h, said stream comprising 0.9461 kg of vanillin per kg of stream ($F_5$).

The stream ($F_7$) is then introduced into distillation column 2 with a feed flow rate of 50.00 kg/h. Its vanillin content is 0.9461 kg/kg.

Column 2 which is used has the following characteristics and operating conditions:

TABLE (III)

| Column 2 | |
|---|---|
| Diameter (mm) | 200 |
| Height (mm) | 2500 |
| Total NTS (number of theoretical stages) reboiler included | 11 |
| NTS (number of theoretical stages) below the feed | 9 |
| Pressure at top of column 2 (mmHg) | 2 |
| Pressure at bottom of column 2 (mmHg) | 7 |
| Temperature at top of column 2 (° C.) | 121 |
| Temperature at bottom of column 2 (° C.) | 171 |
| Load factor $(kg/m^3)^{0.5} \times m \cdot s^{-1}$ | 3.8 |
| Mean relative volatility (VA/heavy compounds) | 8.0 |
| Reflux top of column 2: ($F_9$) after condenser 7 (kg/h) | 12.3 |
| Recycling bottom of column 2: ($F_{12}$) on exchanger 8 (kg/h) | 550 |
| Heat load to the boiler (kcal/h) | 7060 |

At the top of column 2, a gas stream ($F_8$), which after condensation becomes the stream ($F_{10}$), is recovered at a rate of 49.0 kg/h and contains vanillin at a content of 0.9646 kg/kg.

At the bottom of column 2, a liquid stream ($F_{11}$) is withdrawn at a rate of 551.8 kg/h, said stream comprising 0.1260 kg of vanillin per kg of stream ($F_{11}$).

A fraction ($F_{13}$) of the stream ($F_{11}$) feeds the falling-film evaporator 3, the other fraction ($F_{12}$) being reintroduced laterally into distillation column 2.

The characteristics and the operating conditions of the evaporator 3 are collated in table (IV):

TABLE (IV)

| Falling-film evaporator 3 | |
|---|---|
| Number of tubes | 10 |
| Diameter of a tube (mm) | 10 |
| Tube thickness (mm) | 2 |
| Height (mm) | 800 |
| Total exchange surface (m$^2$) | 0.251 |
| Evaporator pressure (mmHg) | 6.6 |
| Heat-transfer fluid temperature (° C.) | 196.5 |
| Average film temperature (° C.) | 194 |
| Average feed viscosity (cPo) | 120 |
| Overall heat transfer coefficient (kcal/hm$^{2°}$ C.) | 173 |
| Heat load of the falling-film evaporator (kcal/h) | 89 |
| Mean relative volatility VA/heavy compounds (mmHg/mmHg) | 8.0 |
| Feed from column 2: ($F_{13}$) (kg/h) | 1.826 |
| VA content in ($F_{13}$) (kg/kg) | 0.126 |
| Total feed ($F_{18}$) (kg/h) | 13.33 |
| VA content in ($F_{18}$) (kg/kg) | 0.0495 |
| Vaporization and recycling to column 2: ($F_{14}$) (kg/h) | 0.826 |
| VA content in ($F_{14}$) (kg/kg) | 0.234 |
| Liquid at bottom of evaporator: ($F_{15}$) (kg/h) | 12.48 |
| VA content in ($F_{15}$) (kg/kg) | 0.037 |
| Recycling to the feed of the falling film: ($F_{16}$) (kg/h) | 11.52 |
| VA content in ($F_{16}$) (kg/kg) | 0.037 |
| Tar extracted: ($F_{17}$) (kg/h) | 0.960 |
| VA content in ($F_{17}$) (kg/kg) | 0.037 |
| VA losses in ($F_{17}$) (kg/h) | 0.037 |
| Falling-film evaporator vaporization rate (% by mass) | 6.5 |
| Falling-film evaporator VA recovery yield (% by mass) | 84.3 |

EXAMPLE 3

In this example, a wiped-film evaporator 9 as illustrated in FIG. 2 is used.

The stream ($F_1$) which feeds column 1 has a vanillin content of 0.6000 kg/kg, a light impurity content of 0.0215 kg/kg and a heavy impurity content of 0.0127 kg/kg.

The stream ($F_1$) is introduced into column 1 with a feed flow rate of 78.84 kg/h.

At the top of column 1, a liquid stream ($F_4$) is recovered, after condensation, at a rate of 28.80 kg/h, said stream no longer containing vanillin.

At the bottom of column 1, a liquid stream ($F_5$) is withdrawn at a rate of 550 kg/h, said stream comprising 0.9461 kg of vanillin per kg of stream ($F_5$).

The stream ($F_7$) is then introduced into distillation column 2 with a feed flow rate of 50.00 kg/h. Its vanillin content is 0.9461 kg/kg.

Column 2 which is used has the following characteristics and operating conditions:

TABLE (V)

| Column 2 | |
|---|---|
| Diameter (mm) | 200 |
| Height (mm) | 2500 |
| Total NTS (number of theoretical stages) reboiler included | 11 |
| NTS (number of theoretical stages) below the feed | 9 |
| Pressure at top of column 2 (mmHg) | 2 |
| Pressure at bottom of column 2 (mmHg) | 9.5 |
| Temperature at top of column 2 (° C.) | 121 |
| Temperature at bottom of column 2 (° C.) | 160 |
| Load factor $(kg/m^3)^{0.5} \times m \cdot s^{-1}$ | 3.9 |
| Mean relative volatility (VA/heavy compounds) | 8.1 |
| Reflux top of column 2: ($F_9$) after condenser 7 (kg/h) | 14.6 |
| Recycling bottom of column 2: ($F_{12}$) on exchanger 8 (kg/h) | 600 |
| Heat load to the boiler (kcal/h) | 6985 |

At the top of column 2, a gas stream ($F_8$), which after condensation becomes the stream ($F_{10}$), is recovered at a rate of 48.8 kg/h and contains vanillin at a content of 0.9646 kg/kg.

At the bottom of column 2, a liquid stream ($F_{11}$) is withdrawn at a rate of 604.9 kg/h, said stream comprising 0.531 kg of vanillin per kg of stream ($F_{11}$).

A fraction ($F_{13}$) of the stream ($F_{11}$) feeds the wiped-film evaporator 9, the other fraction ($F_{12}$) being reintroduced laterally into distillation column 2.

The characteristics and the operating conditions of the evaporator 9 are collated in table (VI):

TABLE (VI)

| Wiped-film evaporator 9 | |
|---|---|
| Number of tubes | 1 |
| Diameter of the tube (mm) | 100 |

TABLE (VI)-continued

Wiped-film evaporator 9

| | |
|---|---|
| Tube thickness (mm) | 4 |
| Height (mm) | 700 |
| Exchange surface (m$^2$) | 0.22 |
| Nature of the moving wiper blades (aluminum) | rollers |
| Rotational speed of the rotor (revs/min) | 300 |
| Evaporator pressure (mmHg) | 2 |
| Heat-transfer fluid temperature (° C.) | 207 |
| Average film temperature (° C.) | 184 |
| Average feed viscosity (cPo) | 120 |
| Overall heat transfer coefficient (kcal/hm$^{2°}$ C.) | 82 |
| Heat load of the wiped-film evaporator (kcal/h) | 398 |
| Mean relative volatility (VA/heavy compounds) | 8.4 |
| Feed from column 2: ($F_{13}$) (kg/h) | 4.877 |
| VA content in ($F_{13}$) (kg/kg) | 0.5305 |
| Total feed ($F_{18}$) (kg/h) | 4.877 |
| VA content in ($F_{18}$) (kg/kg) | 0.5305 |
| Vaporization and recycling to column 2: ($F_{14}$) (kg/h) | 3.678 |
| VA content in ($F_{14}$) (kg/kg) | 0.0641 |
| Liquid at bottom of evaporator: ($F_{19}$) (kg/h) | 1.199 |
| VA content in ($F_{19}$) (kg/kg) | 0.192 |
| Recycling to the feed of the wiped film: ($F_{20}$) (kg/h) | 0 |
| Tar extracted: ($F_{21}$) (kg/h) | 1.199 |
| VA content in ($F_{21}$) (kg/kg) | 0.192 |
| VA losses in ($F_{21}$) (kg/h) | 0.229 |
| Wiped-film evaporator vaporization rate (% by mass) | 75.4 |
| Wiped-film evaporator VA recovery yield (% by mass) | 91.1 |

EXAMPLE 4

In this example, a short-path evaporator (with an internal condenser) 12 as illustrated in FIG. 3 is used.

The stream ($F_1$) which feeds column 1 has a vanillin content of 0.6000 kg/kg, a light impurity content of 0.0215 kg/kg and a heavy impurity content of 0.0127 kg/kg.

The stream ($F_1$) is introduced into column 1 with a feed flow rate of 78.84 kg/h.

At the top of column 1, a liquid stream ($F_4$) is recovered, after condensation, at a rate of 28.80 kg/h, said stream no longer containing vanillin.

At the bottom of column 1, a liquid stream ($F_5$) is withdrawn at a rate of 550 kg/h and comprises 0.9461 kg of vanillin per kg of stream ($F_5$).

The stream ($F_7$) is then introduced into distillation column 2 with a feed flow rate of 50.00 kg/h. Its vanillin content is 0.946 kg/kg.

Column 2 which is used has the following characteristics and operating conditions:

TABLE (VII)

Column 2

| | |
|---|---|
| Diameter (mm) | 200 |
| Height (mm) | 2500 |
| Total NTS (number of theoretical stages) reboiler included | 11 |
| NTS (number of theoretical stages) below the feed | 9 |
| Pressure at top of column 2 (mmHg) | 2 |
| Pressure at bottom of column 2 (mmHg) | 9.5 |
| Temperature at top of column 2 (° C.) | 121 |
| Temperature at bottom of column 2 (° C.) | 174 |
| Load factor (kg/m$^3$)$^{0.5}$ × m · s$^{-1}$ | 4.3 |

TABLE (VII)-continued

Column 2

| | |
|---|---|
| Mean relative volatility (VA/heavy compounds) | 8.1 |
| Reflux top of column 2: ($F_9$) after condenser 7 (kg/h) | 14.7 |
| Recycling bottom of column 2: ($F_{12}$) on exchanger 8 (kg/h) | 500 |
| Heat load to the boiler (kcal/h) | 7500 |

At the top of column 2, a gas stream ($F_8$), which after condensation becomes the stream ($F_{10}$), is recovered at a rate of 48.99 kg/h and contains vanillin at a content of 0.9648 kg/kg.

At the bottom of column 2, a liquid stream ($F_{11}$) is withdrawn at a rate of 503.3 kg/h, said stream comprising 0.1898 kg of vanillin per kg of stream ($F_{11}$).

A fraction ($F_{13}$) of the stream ($F_{11}$) feeds the short-path evaporator with internal condenser 12, the other fraction ($F_{12}$) being reintroduced laterally into distillation column 2.

The characteristics and the operating conditions of the evaporator 12 are collated in table (VIII):

TABLE (VIII)

Short-path evaporator with internal condenser 12

| | |
|---|---|
| Number of tubes | 1 |
| Diameter of the tube (mm) | 90 |
| Tube thickness (mm) | 4 |
| Height (mm) | 170 |
| Exchange surface (m$^2$) | 0.048 |
| Nature of the moving wiper blades (Teflon) | rollers |
| Rotational speed of the rotor (revs/min) | 350 |
| Evaporator pressure (mmHg) | 4 |
| Heat-transfer fluid temperature (° C.) | 222 |
| Average film temperature (° C.) | 192 |
| Average feed viscosity (cPo) | 120 |
| Overall heat transfer coefficient (kcal/hm$^{2°}$ C.) | 91 |
| Heat load of the wiped-film evaporator (kcal/h) | 118 |
| Mean relative volatility (VA/heavy compounds) | 7.9 |
| Feed from column 2: ($F_{13}$) (kg/h) | 3.313 |
| VA content in ($F_{13}$) (kg/kg) | 0.1897 |
| Vaporization and recycling to column 2: ($F_{14}$) (kg/h) | 2.304 |
| VA content in ($F_{14}$) (kg/kg) | 0.2552 |
| Liquid at bottom of evaporator: ($F_{15}$) (kg/h) | 1.009 |
| VA content in ($F_{15}$) (kg/kg) | 0.0404 |
| Tar extracted: ($F_{15}$) (kg/h) | 1.009 |
| VA content in ($F_{15}$) (kg/kg) | 0.0404 |
| VA losses in ($F_{15}$) (kg/h) | 0.0404 |
| Vaporization rate in the short-path evaporator with internal condenser (% by mass) | 69 |
| VA recovery yield of short-path evaporator with internal condenser (% by mass) | 93.56 |

EXAMPLE 5

In this example, a horizontal wiped-film evaporator 16 (rotor with self-cleaning fixed blades) as illustrated in FIG. 4 is used.

The stream ($F_1$) which feeds column 1 has a vanillin content of 0.6000 kg/kg, a light impurity content of 0.0215 kg/kg and a heavy impurity content of 0.0127 kg/kg.

The stream ($F_1$) is introduced into column 1 with a feed flow rate of 78.84 kg/h.

At the top of column 1, a liquid stream ($F_4$) is recovered, after condensation, at a rate of 28.80 kg/h, said stream no longer containing vanillin.

At the bottom of column 1, a liquid stream ($F_5$) is withdrawn at a rate of 500 kg/h and comprises 0.9461 kg of vanillin per kg of stream ($F_5$).

The stream ($F_7$) is then introduced into distillation column 2 with a feed flow rate of 50.00 kg/h. Its vanillin content is 0.9461 kg/kg.

Column 2 which is used has the following characteristics and operating conditions:

TABLE (IX)

| Column 2 | |
|---|---|
| Diameter (mm) | 200 |
| Height (mm) | 2500 |
| Total NTS (number of theoretical stages) | 11 |
| NTS (number of theoretical stages) below the feed | 9 |
| Pressure at top of column 2 (mmHg) | 2 |
| Pressure at bottom of column 2 (mmHg) | 9.5 |
| Temperature at top of column 2 (° C.) | 120 |
| Temperature at bottom of column 2 (° C.) | 162 |
| Load factor $(kg/m^3)^{0.5} \times m \cdot s^{-1}$ | 3.9 |
| Mean relative volatility (VA/heavy compounds) | 8.1 |
| Reflux top of column 2: ($F_9$) after condenser 7 | 15.0 |
| Recycling bottom of column 2: ($F_{12}$) on exchanger 8 | 400 |
| Heat load to the reboiler (kcal/h) | 7000 |

At the top of column 2, a gas stream ($F_8$), which after condensation becomes the stream ($F_{10}$) is recovered at a rate of 49.0 kg/h and contains vanillin at a content of 0.9654 kg/kg.

At the bottom of column 2, a liquid stream ($F_{11}$) is withdrawn at a rate of 404.9 kg/h, said stream comprising 0.531 kg of vanillin per kg of stream ($F_{11}$).

A fraction ($F_{13}$) of the stream ($F_{11}$) feeds the fixed-blade horizontal wiped evaporator 16, the other fraction ($F_{12}$) being reintroduced laterally into distillation column 2.

The characteristics and the operating conditions of the evaporator 16 are collated in table (X):

TABLE (X)

| Fixed-blade horizontal wiped-film 16 | |
|---|---|
| Body diameter (mm) | 170 |
| Rotor diameter (mm) | 120 |
| Tube thickness (mm) | 2 |
| Length (mm) | 500 |
| Total wall + rotor exchange surface (m²) | 0.30 |
| Nature of the fixed wiper blades (AISI 316 steel) | profiled |
| Rotational speed of the rotor (revs/min) | 50 |
| Evaporator pressure (mmHg) | 2 |
| Heat-transfer fluid temperature (° C.) | 195 |
| Average film temperature (° C.) | 183.5 |
| Average feed viscosity (cPo) | 120 |
| Overall heat transfer coefficient (kcal/hm²° C.) | 149 |
| Heat load of the wiped-film evaporator (kcal/h) | 496 |
| Mean relative volatility (VA/heavy compounds) | 8.0 |
| Feed from column 2: ($F_{13}$) (kg/h) | 4.877 |
| VA content in ($F_{13}$) (kg/kg) | 0.5310 |
| Vaporization and recycling to column 2: ($F_{14}$) (kg/h) | 3.866 |
| VA content in ($F_{14}$) (kg/kg) | 0.6614 |
| Liquid at evaporator output, tar extracted: ($F_{15}$) (kg/h) | 1.011 |
| VA content in ($F_{15}$) (kg/kg) | 0.0320 |
| VA losses in ($F_{15}$) (kg/h) | 0.032 |
| Horizontal wiped-film evaporator vaporization rate (% by mass) | 79.3 |
| Horizontal wiped-film evaporator VA recovery yield (% by mass) | 98.8 |

The invention claimed is:

1. A process for separating and recovering an aromatic aldehyde from a mixture comprising an aromatic aldehyde, light and heavy impurities and tar, comprising:
   obtaining said mixture comprising said aromatic aldehyde, said light and heavy impurities and tar by extraction using an organic solvent, carried out after introduction of a formyl group, and then separating said aromatic aldehyde from said organic solvent used in said extraction by carrying out a distillation, to obtain:
   at the distillation bottom, a liquid phase comprising said aromatic aldehyde accompanied by various light impurities, the tar and heavy impurities,
   at the distillation top, a gas phase comprising said organic solvent used in said extraction and said aromatic aldehyde at a low concentration enabling recycling of the organic solvent to said extraction; and
   introducing a liquid stream including said mixture obtained from said distillation bottom into an evaporator, said mixture being vaporized therein such that, on the one hand, a gas stream comprising the aromatic aldehyde, the light impurities, the heavy impurities that are vaporized at selected evaporation temperature and pressure, and, on the other hand, a liquid stream essentially comprising the tar are separated, and recovering the aromatic aldehyde from the separated gas stream,
   said aromatic aldehyde having the following formula (I):

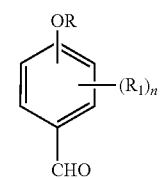

(I)

wherein in said formula (I):
   R is a hydrogen atom or an alkyl group,
   $R_1$ radicals, which are identical or different, are each a hydrogen atom, a hydroxyl group, an alkyl radical, or an alkoxy radical, and
   n is a number ranging from 0 to 4.

2. The process as defined by claim 1, wherein said mixture which is introduced into said evaporator comprises from 55% to 94% by weight of an aromatic aldehyde, and from 6% to 45% by weight of light and heavy impurities, and tar.

3. The process as defined by claim 1, wherein a fraction of the separated gas stream essentially comprising the aromatic aldehyde obtained from said evaporation is recycled in gaseous state or after condensation, to a step upstream of such separation step by evaporation.

4. The process as defined by claim 1, wherein a fraction of the separated liquid stream comprising tar obtained from said evaporator is recycled to the evaporator.

5. The process as defined by claim 1, wherein the liquid stream obtained at the distillation bottom is concentrated before being introduced into the evaporator.

6. The process as defined by claim 5, wherein the liquid stream obtained at the distillation bottom is concentrated by another distillation such as to obtain:
   at bottom of said other distillation, the aromatic aldehyde accompanied by the tar and heavy impurities,
   at top of said other distillation, a gas phase essentially comprising the aromatic aldehyde, the light impurities and heavy impurities at a content of less than 100 ppm.

7. The process as defined by claim 6, further comprising recycling a fraction of said gas stream essentially containing the aromatic aldehyde obtained from said other distillation top, in gaseous state or after condensation, to said concentrating step using said other distillation.

8. The process as defined by claim 1, wherein the vaporization of said mixture is carried out in a falling-film evaporator.

9. The process as defined by claim 8, wherein the vaporization rate, expressed by the weight ratio from the obtained gas stream to the evaporator feed stream ranges from 5% to 75%.

10. The process as defined by claim 8, wherein the separated liquid stream comprising the tar is recycled at a recycling rate of 50% to 75%.

11. The process as defined by claim 1, wherein the vaporization of said mixture is carried out in a wiped-film evaporator.

12. The process as defined by claim 11, wherein the vaporization rate, expressed by the weight ratio from the obtained gas stream to the evaporator feed stream ranges from 20% to 90%.

13. The process as defined by claim 11, wherein the separated liquid stream comprising the tar is recycled at a recycling rate of 0% to 50%.

14. The process as defined by claim 1, wherein the vaporization of said mixture is carried out in a short path evaporator with an internal condenser.

15. The process as defined by claim 14, wherein the vaporization rate, expressed by the weight ratio from the obtained gas stream to the evaporator feed stream ranges from 10% to 95%.

16. The process as defined by claim 14, wherein the separated liquid stream comprising the tar is recycled at a recycling rate of 0% to 50%.

17. The process as defined by claim 1, wherein the vaporization of said mixture is carried out in a horizontal wiped evaporator.

18. The process as defined by claim 17, wherein the vaporization rate, expressed by the weight ratio from the obtained gas stream to the evaporator feed stream ranges from 10% to 90%.

19. The process as defined by claim 17, wherein the separated liquid stream comprising the tar is recycled at a recycling rate of 0% to 50%.

20. The process as defined by claim 1, being carried out under an inert gas atmosphere, optionally under a nitrogen atmosphere.

21. The process as defined by claim 1, wherein the aromatic aldehyde comprises one of the following aldehydes selected from the group consisting of:
 vanillin,
 ethylvanillin (3-ethoxy-4-hydroxybenzaldehyde),
 isovanilline (4-methoxy-3-hydroxybenzaldehyde),
 o-vanillin (3-methoxy-2-hydroxybenzaldehyde),
 protocatechualdehyde,
 syringic aldehyde (3,5-dimethoxy-4-hydroxybenzaldehyde),
 veratric aldehyde (3,4-dimethoxybenzaldehyde), and
 p-hydroxybenzaldehyde.

22. The process as defined by claim 21, wherein the aromatic aldehyde comprises vanillin and ethylvanillin.

* * * * *